United States Patent [19]
Benecke et al.

[11] Patent Number: 6,068,624
[45] Date of Patent: May 30, 2000

[54] ENDOSCOPIC INSTRUMENT WITH OVERLOAD PROTECTION

[75] Inventors: Rainer Benecke, Todendorf; Manfred Moeller, Hamburg, both of Germany

[73] Assignee: Olympus Winter & Ibe GmbH, Hamburg, Germany

[21] Appl. No.: 09/306,527

[22] Filed: May 6, 1999

[30] Foreign Application Priority Data

Jun. 19, 1998 [DE] Germany ..................... 298 10 958 U

[51] Int. Cl.$^7$ ............................. A61B 1/00; A61B 17/00
[52] U.S. Cl. ............................ 606/1; 600/104; 600/101; 600/130; 600/143
[58] Field of Search .................................. 600/104, 143, 600/130, 136, 101, 118, 149; 606/1

[56] References Cited

U.S. PATENT DOCUMENTS

| | | | |
|---|---|---|---|
| 5,299,559 | 4/1994 | Bruce et al. | 128/4 |
| 5,349,942 | 9/1994 | Heimberger | 126/4 |
| 5,643,248 | 7/1997 | Yoon | 606/1 |

*Primary Examiner*—Linda C. M. Dvorak
*Assistant Examiner*—Jocelyn Debra Ram
*Attorney, Agent, or Firm*—Pearne, Gordon, McCoy & Granger LLP

[57] ABSTRACT

A stemmed endoscopic instrument has a distal operational tool, a proximal drive unit and a stem containing a force transmitting element extending through and displaceably received in the stem. A distal end of the force transmitting element acts on the operational tool and a proximal end engages the drive unit so that the force transmitting element drives the operational tool when the drive unit is actuated. An overload protection device limiting the traction force transmissible from the drive unit to the tool has a coupling with two mutually detachably connected coupling elements, the coupling being adjusted so that when a defined tension or force threshold is exceeded, the coupling elements separate from each other and force transmission is interrupted. The overload protection device has two coupling elements (18, 19; 20, 200/290, 280; 300) movable into a mutually geometrically locked position, at least one of the coupling elements being elastically deformable to release, by being reversibly deformed, the other element when the threshold force is exceeded.

4 Claims, 3 Drawing Sheets

ENDOSCOPIC INSTRUMENT WITH OVERLOAD PROTECTION

FIELD OF THE INVENTION

The present invention relates to a stemmed endoscopic instrument with a distal operational tool, a proximal drive unit, a force transmitting element passing through and displaceably received in the stem, the distal end of the force transmitting element acting on the operational tool and its proximal end engaging the drive unit to drive the operational tool and with an overload protection device limiting the transmissible traction force.

BACKGROUND OF THE INVENTION

Stemmed instruments of this type comprise a distal tool and a proximal drive unit. A stem extends between the operational tool and the drive unit and receives a longitudinally displaceable force-transmitting element. The distal end of the force-transmitting element acts on the operational tool and the proximal end engages the drive unit. When a tensile load is applied by actuating the drive unit, the force-transmitting element is shifted inside the stem and thereby actuates the operational tool.

Furthermore, an overload protection device is present in the force-transmission path to limit the transmissible tensile force. This overload protection device is designed to protect the apparatus from damage in the event of excessive traction applied through the drive unit, in particular from destroying the operational tool. Excessive tensile stress of an operational tool, for instance in the form of tongs of which the bearing shaft would break, absolutely must be precluded. If such a rupture were to occur during surgery, there would be danger that the tong elements, no longer securely held, would drop and might seriously injure the patient.

In this respect, it is known from German patent 1,964,896 to use a coupling with coupling elements as the overload protection device, where the coupling elements are kept magnetically engaged. Retention by the magnet used is selected in such manner that if the set limit force is exceeded, the coupling elements disengage from each other, interrupting the force transmission between the drive unit and the operational tool in an impulsive manner. This known apparatus entails complex manufacture.

SUMMARY OF THE INVENTION

An object of the present invention is to provide a stemmed endoscopic instrument fitted with an easily manufactured overload protection device of which the coupling elements, once separated in the event of overload, can easily be reconnected again.

This object is achieved by an apparatus comprising a coupling acting to protect against overload which is a detent coupling. The coupling used for overload protection in the invention comprises two coupling elements which can be mutually engaged in a geometrically locking manner, for instance by being merely plugged or guided into one another, and which in the below-threshold range, that is below a defined limit tensile force exerted on the operational tool, will remain in force-transmitting engagement. Furthermore, at least one of the coupling elements is elastically deformable in such a way that, when a predetermined threshold tensile force is exceeded, it will reversibly deform to release the other element, as a result of which the force-transmitting path between the drive unit and the operational tool is impulsively interrupted.

Immediately after the coupling is separated due to overload, the at least one elastic coupling element returns into its initial shape and thereupon can again be made to geometrically lock with the other element, and thereupon the instrument is at once again ready for use.

In theory, the coupling of the invention used as the overload protection device can be present anywhere in the force transmission path. Illustratively, the coupling may be mounted in the force transmitting element. In such a design, in the event of the threshold force being exceeded, the force transmitting element would be separated longitudinally and thus the force would be interrupted.

Advantageously, however, the coupling is integrated in a zone of the instrument that already comprises a two-component connection. In this case, the connection area need only be modified for the desired coupling of the invention instead of incurring, as is the case illustratively when fitting the coupling into the force transmitting element, the need for completely new and additional components.

It is especially advantageous in this respect that the coupling is implemented between the drive element and the proximal end of the force transmitting element. The proximal end of the force transmitting element frequently comprises a spherical mating element that can be laterally inserted into a slotted, cross-sectionally circular borehole in the drive unit (the slot is crossed by the distally running force transmitting element). The borehole is present in a zone of the drive unit, said zone being adjustable in the longitudinal stem direction, typically the distal end of a pivotable lever, and as a result, after the mating ball has been inserted into the borehole, and the lever is pivoted, the force transmitting element can be displaced in the stem in its longitudinal direction.

In a preferred embodiment of the invention, the borehole illustratively comprises elastically deforming zones which, when overloaded, will widen the slot passing through the borehole so that the mating ball is able to pass through. In another embodiment, the mating ball, or the mating element inserted into the borehole, is elastically deformable such that it deforms under overload and can pass through the slot in the direction of traction. In both embodiments, coupling separation is very simply implemented in practice between the force transmitting element and the drive unit under overload. The separable coupling used as the overload protection device in this embodiment being especially accessible and being composed of components basically known to the surgeon, no problems are encountered after triggering the overload protection device to restore coupling engagement. To restore instrument operability following overload protection triggering, precisely those steps are required which anyway are known to the surgeon from instrument assembly.

Illustratively, the force transmitting element may be a traction wire. Conventionally, however, the element used is able to transmit both thrust and traction, for instance to transmit the force required to close and open the tongs. Therefore, in a preferred embodiment, the force transmitting element of the instrument of the invention also is able to transmit thrust and traction.

BRIEF DESCRIPTION OF THE DRAWINGS

The invention is described below with reference to drawings showing three illustrative embodiments, wherein.

DESCRIPTION OF PREFERRED EMBODIMENTS

Figure 1:
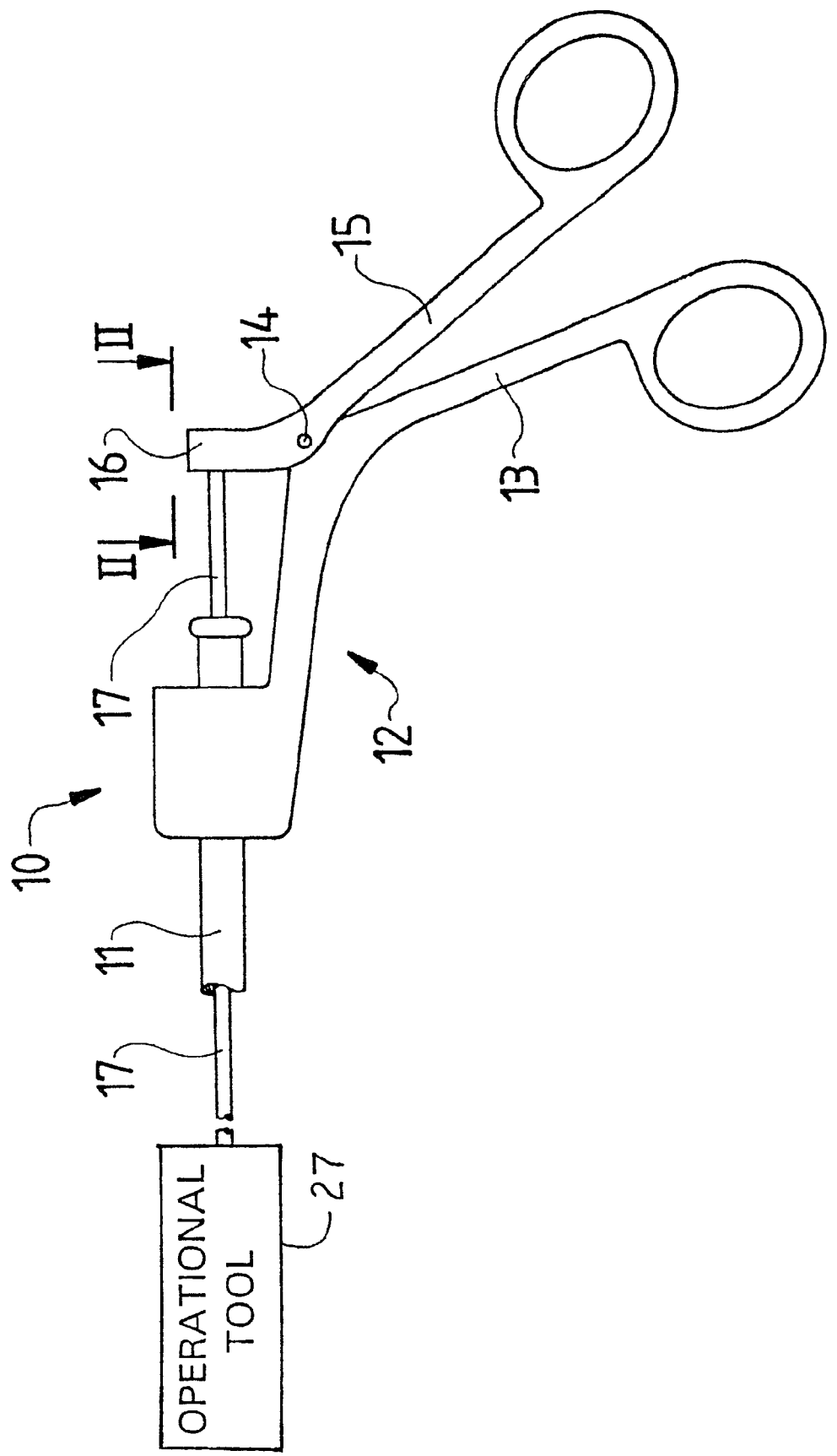
FIG. 1 is an overall side view of the proximal end of a stemmed endoscopic implement.

FIG. 1 shows the proximal portion of a stemmed endoscopic implement 10, a stem 11 being partly shown and comprising a drive unit 12 mounted at its proximal end. Drive unit 12 has conventional scissors grips having a lateral grip arm 13 affixed to the instrument and an arm 15 resting and pivoting about arm 13 in a hinge 14. Distally from hinge 14, the grip arm 15 is formed as a lever 16 which, when the arm 15 is moved, is displaced toward or away from the direction of stem 11.

FIG. 1 only shows a small portion of stem 1, the larger portion extending to an operational tool 27, such as tongs, at its distal end.

A force transmitting element, typically a thrust and traction rod 17, is slidably received in stem 11 and extends between the operational tool and lever 16 of pivotable arm 15. Again, only a proximal portion of thrust and traction rod 17 is shown.

As discussed above, when arm 15 pivots, lever 16 is displaced in the direction of the axis of stem 11 and in the process moves thrust and traction rod 17 and thereby the omitted operational tool.

Figure 2:
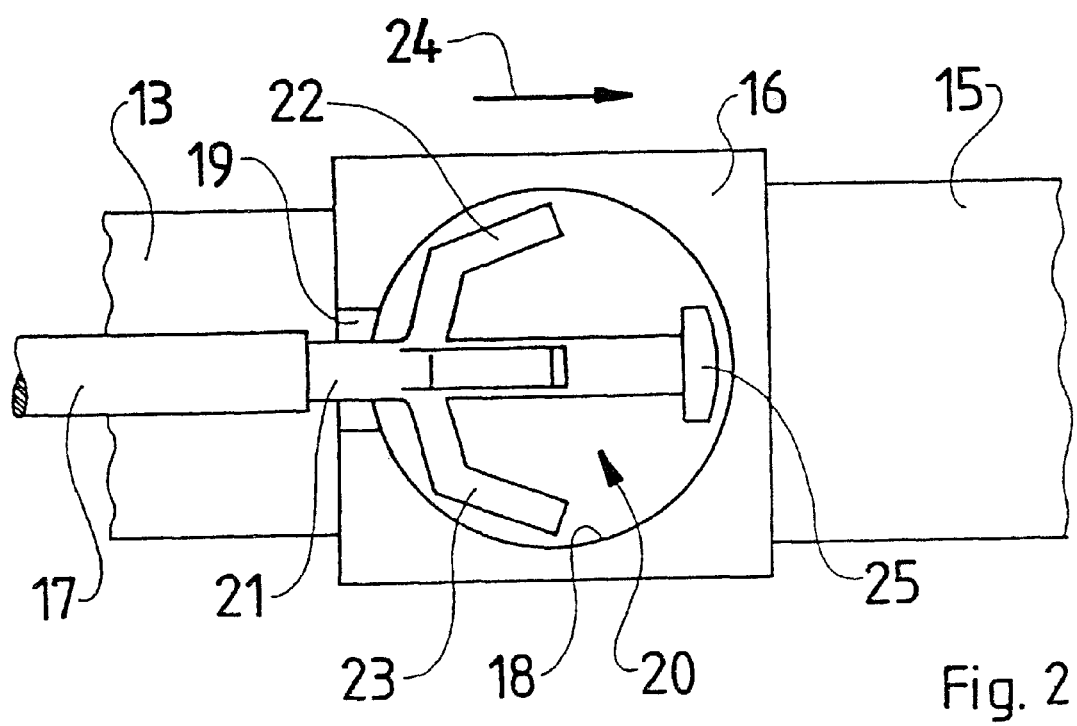
FIG. 2 is a partial top view in the direction of the arrow in the vicinity of the line II—II in FIG. 1.

The overload protection device cannot be seen in FIG. 1. FIG. 2 is needed in that respect, showing the free end of lever 16. Lever 16 has a longitudinal borehole 18 comprising a distal slot 19. Thrust and traction element 17 is geometrically locked by a mating element 20 inside borehole 18.

Mating element 20 is connected by a fitting 21 to thrust and traction rod 17, the dimensions of fitting 21 being such as to allow it to pass through slot 19. Mating element 20 comprises several elastically deformable distal fingers 22, 23 etc. which, in the event of excessive tension are compressed inwardly and then allow all of mating element 20 to pass through slot 19. In case of excessive force, lever 16 is displaced in the direction of arrow 24 against the resistance of thrust and traction rod 17.

Mating element 20 furthermore comprises a pressure absorbing element 25 acting as a pressure support (the lever 16 being displaced against the direction of the arrow 24). Preferably, pressure-absorbing element 25 is dimensioned also to be able to pass through slot 19.

If lever 16 is under excessive tensile load, mating element 20 thus disengages from the borehole 18 and force transmission is impulsively interrupted.

To return implement 10 to operation, only mating element 20 need be inserted again into slot 19, i.e., into borehole 18. Thereupon, the implement is at once operational again.

Figure 3:
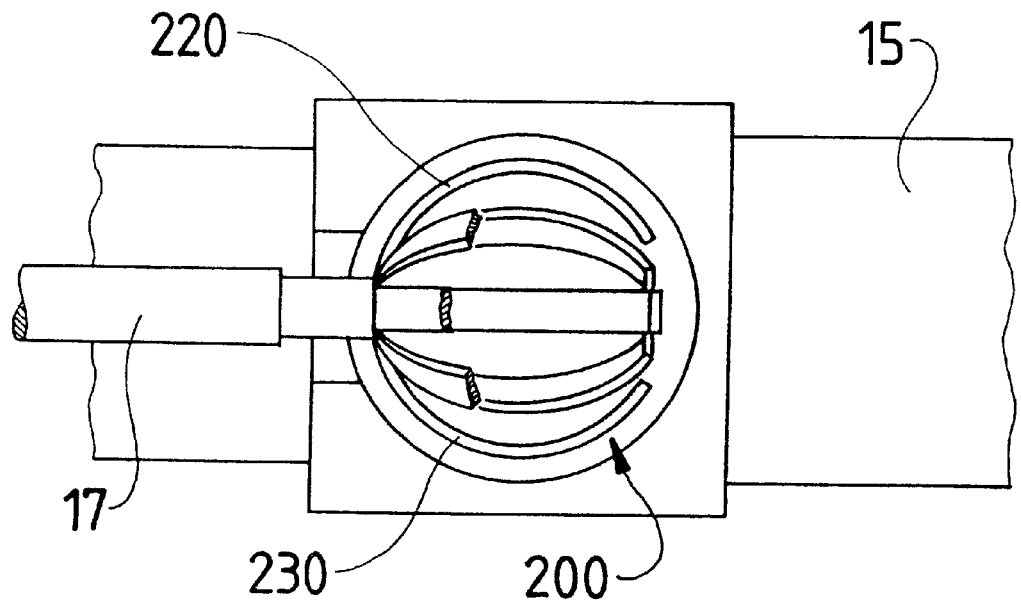
FIGS. 3 and 4 are views similar to FIG. 2 of further illustrative embodiments of couplings applicable to the invention.

FIG. 3 is a view similar to that of FIG. 2 of another illustrative embodiment of an overload protection device in accordance with the invention. The essential difference here is that a mating element 200 has elastically yieldable fingers 220, 230 etc. which however, contrary to the above described embodiment, also can act as a pressure support. This embodiment therefore does not require a separate pressure-absorbing element. In other ways, this embodiment operates exactly as that shown with reference to FIG. 2.

Figure 4:
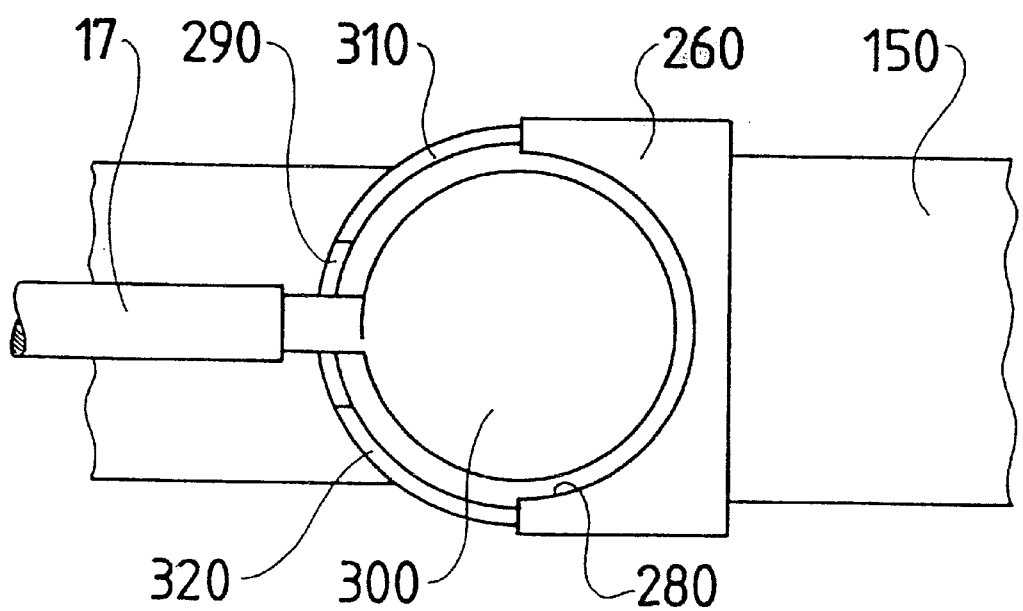

Lastly, in the embodiment of FIG. 4, the principle of operation is reversed. Again, there is a thrust and traction rod 17 at the proximal end of which, however, now there is a rigid, not an elastically deforming, spherical mating element 300. Mating element 300 is anchored in the pivotable end of a lever 260 of a grip arm 150. In this embodiment also there is a circular longitudinal borehole 280 with a longitudinal slot 290 in the end of lever 260. But the main difference is that the distal zone of borehole 280 is not rigid, but rather is made of elastically yielding segments 310 and 320. In the event of excessive tensile load, the distal regions of mating element 300 press so hard against the correspondingly designed wall segments 310 and 320 that the wall segments are spread apart and widen slot 290 sufficiently to permit mating element 300 to disengage from borehole 280. In this instance as well, the force transmission is then suddenly interrupted. The elastic properties of wall segments 310 and 320 are such that they immediately resume their initial shapes and thereupon the geometric locking between the mating element 300 and the borehole 280 will be restored.

It is understood that there is a number of further possible embodiments of the invention. Conceivably, the coupling may be placed in the zone of the thrust and traction rod. Theoretically as well, the coupling may be located in the transition range to the operational tool. Obviously too, both coupling elements may be fitted with deforming zones.

What is claimed is:

1. A stemmed endoscopic instrument comprising a distal operational tool;

a proximal drive unit;

a stem containing a force transmitting element extending through and displaceably received in said stem, a distal end of said force transmitting element acting on said operational tool and a proximal end engaging said drive unit so that said force transmitting element drives said operational tool by means of the drive unit;

an overload protection device limiting the transmissible traction force and having a coupling with two mutually detachably connected coupling elements, said coupling being adjusted so that, when a defined tension threshold is exceeded, said coupling elements separate from each other and force transmission is interrupted, said two coupling elements of said overload protection device being movable into a mutually geometrically locked position, at least one of said coupling elements being elastically deformable to release, by being reversibly deformed, another of said elements when the threshold tensile force is exceeded.

2. An endoscopic instrument according to claim 1 wherein said coupling elements are located between said drive unit (12) and said force transmitting device (17).

3. An endoscopic instrument according to claim 2, wherein said drive unit comprises a longitudinal borehole (18, 280) having a longitudinal slot (19, 290) and forming one coupling element, and in that a mating element (20, 200, 300) insertable in geometrically locking manner in said borehole (18, 280) forms the other coupling element at the force transmitting element (17).

4. An endoscopic implement according to claim 1 wherein said force transmitting element (17) is a thrust and traction element (17).

* * * * *

UNITED STATES PATENT AND TRADEMARK OFFICE
CERTIFICATE OF CORRECTION

PATENT NO. : 6,068,624
DATED : May 30, 2000
INVENTOR(S) : Benecke et al.

It is certified that error appears in the above-identified patent and that said Letters Patent is hereby corrected as shown below:

```
On Title Page, Section [30], Foreign Application
    Priority Data, delete "298 10 958 U"
    and insert --298 10 958.1--.
```

Signed and Sealed this

Third Day of April, 2001

*Attest:*

NICHOLAS P. GODICI

*Attesting Officer*     *Acting Director of the United States Patent and Trademark Office*